US00PP24137P3

(12) United States Plant Patent
Leis et al.

(10) Patent No.: US PP24,137 P3
(45) Date of Patent: Jan. 7, 2014

(54) APPLE TREE NAMED 'SMERALDA'

(50) Latin Name: *Malus domestica Mill.*
Varietal Denomination: Smeralda

(75) Inventors: Michelangelo Leis, Ferrara (IT); Alessio Martinelli, Ferrara (IT); Francesco Tagliani, Argenta (IT); Gianfranco Castagnoli, Quingentole (IT); Donata Azzolini, legal representative, Quingentole (IT); Pietro Castagnoli, legal representative, Quingentole (IT); Alessandro Castagnoli, legal representative, Quingentole (IT)

(73) Assignee: C.I.V.—Consorzio Italiano Vivaisti—Societa Consortile a R.L., Comacchio FE (IT)

( * ) Notice: Subject to any disclaimer, the term of this patent is extended or adjusted under 35 U.S.C. 154(b) by 27 days.

(21) Appl. No.: 13/374,437

(22) Filed: Dec. 29, 2011

(65) Prior Publication Data

US 2013/0031685 P1 Jan. 31, 2013

(30) Foreign Application Priority Data

Jul. 26, 2011 (QZ) ..... PBR 20111880

(51) Int. Cl.
*A01H 5/00* (2006.01)

(52) U.S. Cl.
USPC ..... Plt./172

(58) Field of Classification Search
USPC ..... Plt./172, 161
See application file for complete search history.

*Primary Examiner* — Kent L Bell
(74) *Attorney, Agent, or Firm* — Foley & Lardner LLP

(57) ABSTRACT

A new and distinct *Malus domestica* Mill. apple tree named 'Smeralda' particularly characterized by having a compact habit with short branches and therefore very easy to manage. Precocious fruit bearing. Consistent high productivity with no tendency to biennial bearing. Resistant to scab. The ripening time is 30 days before 'Granny Smith'. The fruit is medium-large with a smooth, uniform green color. The fine, crispy, juicy, pleasant flesh is yellow with an excellent flavour, feeling fresh in the mouth because of its high sugar content and elevated acidity. The taste is similar to 'Granny Smith' but sweeter and more fragrant. Long storage capacity and long shelf life.

4 Drawing Sheets

Latin name of the genus and species of the plant claimed: *Malus domestica* Mill.

Variety denomination: 'Smeralda'.

PRIORITY CLAIM

This application claims priority to European Community Plant Variety Office Application No. 2011/1880, filed Jul. 26, 2011.

BACKGROUND OF THE INVENTION

The present invention relates to a new and distinct variety of apple tree, botanically known as *Malus domestica* Mill. of the Family Rosaceae, and hereinafter referred to by the variety denomination 'Smeralda'.

The new *Malus* variety is a product of a planned breeding program conducted by the inventors, Michelangelo Leis, Alessio Martinelli, Gianfranco Castagnoli and Francesco Tagliani in S. Giuseppe di Comacchio (Ferrara), Italy. The objective of the breeding program was to develop new *Malus* varieties with improved production characteristics, high-quality flavour and aroma, and sustainability by increasing the tree's natural resistance. The primary objective of the research programme is to selection new apple varieties with natural resistances, in particular to scab.

The new *Malus* variety, 'Smeralda' originated from a cross made in a planned, controlled breeding program in S. Giuseppe di Comacchio (Ferrara), Italy. The female parent is an unpatented selection denominated 'DA-85'. The male parent is an unpatented selection denominated 'B9-5'. 'Smeralda' was discovered and selected in September 2005 by the inventors as a flowering plant within the progeny of the stated cross in a controlled environment in S. Giuseppe di Comacchio (Ferrara), Italy.

Asexual reproduction of the new *Malus* variety by budding and grafting was first performed in September 2005 and in the following years in S. Giuseppe di Comacchio (Ferrara), Italy, and has demonstrated that the combination of characteristics as herein disclosed for the new *Malus* variety are firmly fixed and retained through successive generations of asexual reproduction. The new variety reproduces true to type.

In comparison to the parents 'Smeralda' differs primarily in the traits listed in Table 1.

TABLE 1

Comparison to parent varieties

| Characteristic in which the variety is different | State of expression of candidate variety | The female parent (DA-85) | The male parent (B9-5) |
|---|---|---|---|
| Resistance to scab | Yes | Not | Yes |
| Fruit: color | Green | Red | Yellow |
| Fruit: size | Medium to large | Medium | Medium |
| Time of eating maturity | Medium to late | Medium | Late to very late |

BRIEF DESCRIPTION OF THE INVENTION

The following traits have been repeatedly observed and are determined to be unique characteristics of 'Smeralda' which in combination distinguish this apple tree as a new and distinct variety:

1. Green skin color fruit;
2. Scab resistance;
3. Compact habit and short branches, easy to manage and
4. High sugar content and elevated acidity, that give a balanced flavor.

In comparison to the similar variety 'Granny Smith', 'Smeralda' differs primarily in the traits listed in Table 2:

TABLE 2

| Comparison with similar variety | | | |
|---|---|---|---|
| Denomination of similar variety | Characteristic in which the similar variety is different | State of expression of similar variety | State of expression of candidate variety |
| 'Granny Smith' | Time of eating maturity | Very late | Medium to late |
| | Color of flesh | Greenish | Cream |
| | Resistance to disease | No | Scab resistant |

Of the commercial cultivars known to the inventors, the most similar in comparison to 'Smeralda' is variety 'Granny Smith' as compared in Table 2.

BRIEF DESCRIPTION OF THE DRAWINGS

The accompanying photographs illustrate the overall appearance of the new apple tree 'Smeralda' showing the colors as true as is reasonably possible with color reproductions of this type. Color in the photographs may differ slightly from the color value cited in the detailed botanical description, which accurately describe the color of 'Smeralda'. In some photographs the label shows the breeder's reference 'A7B9-119'.

DETAILED BOTANICAL DESCRIPTION

Figure 1:
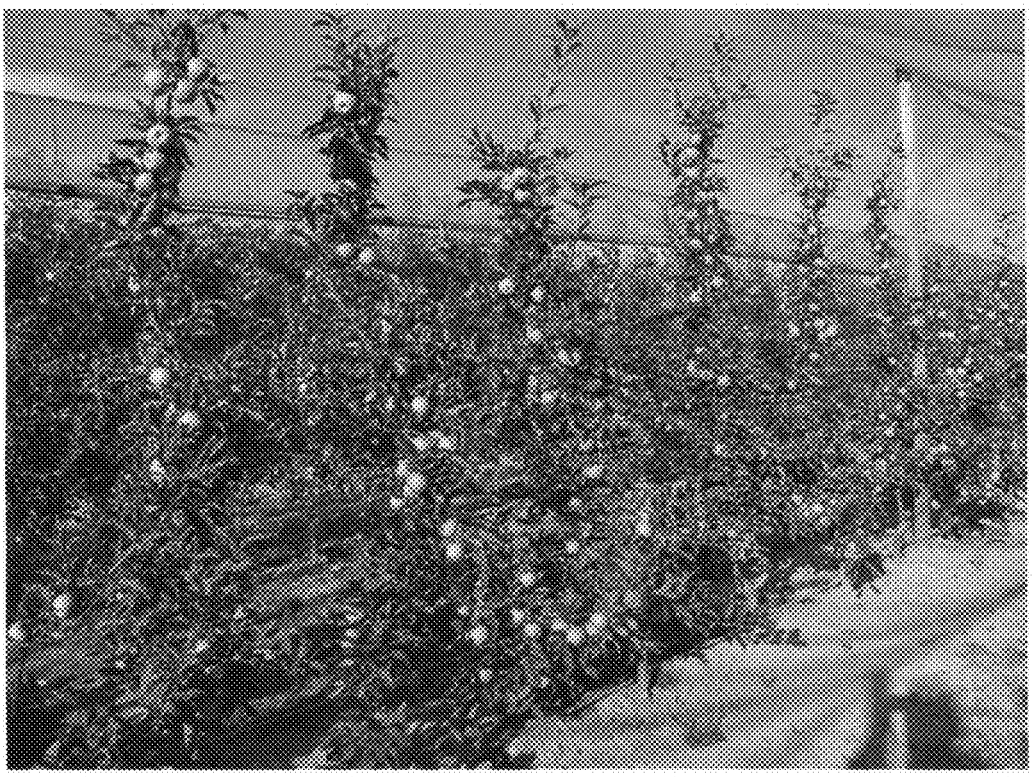
FIG. 1: illustrates the tree of 'Smeralda'.
Figure 2:
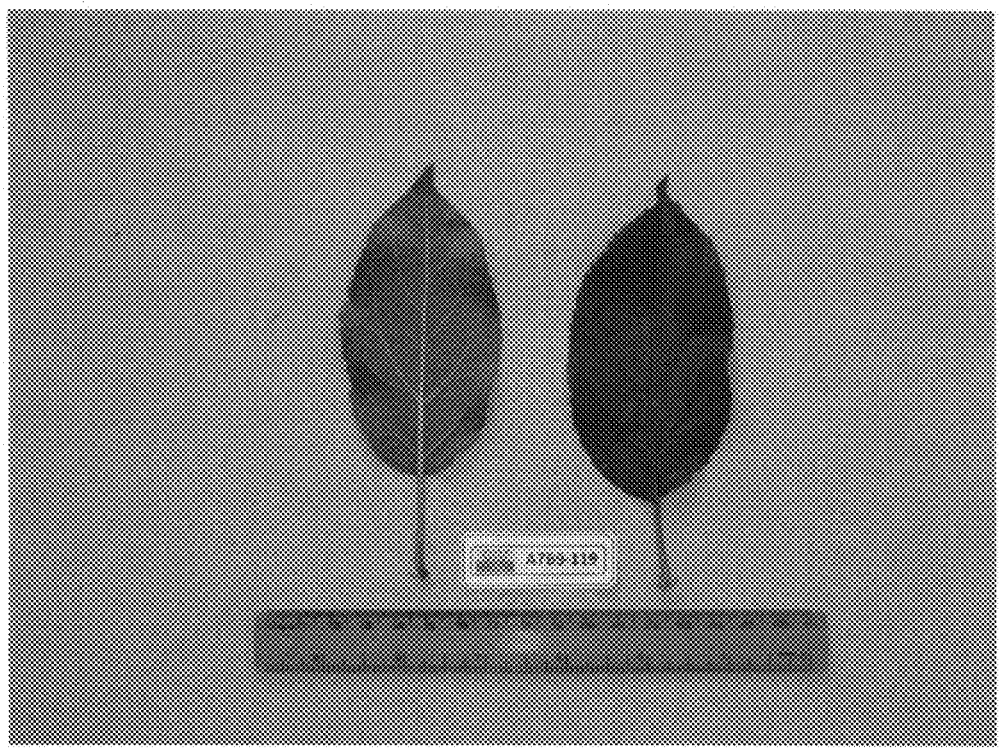
FIG. 2: illustrates the leaves of 'Smeralda'.
Figure 3:
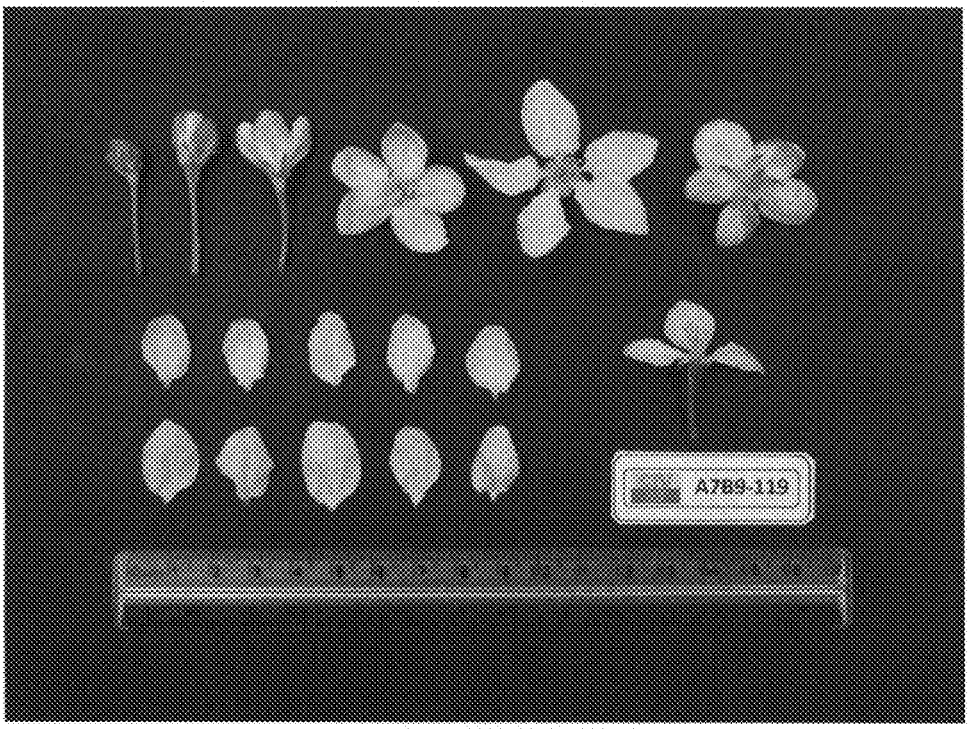
FIG. 3: illustrates the flowers of 'Smeralda'.
Figure 4:
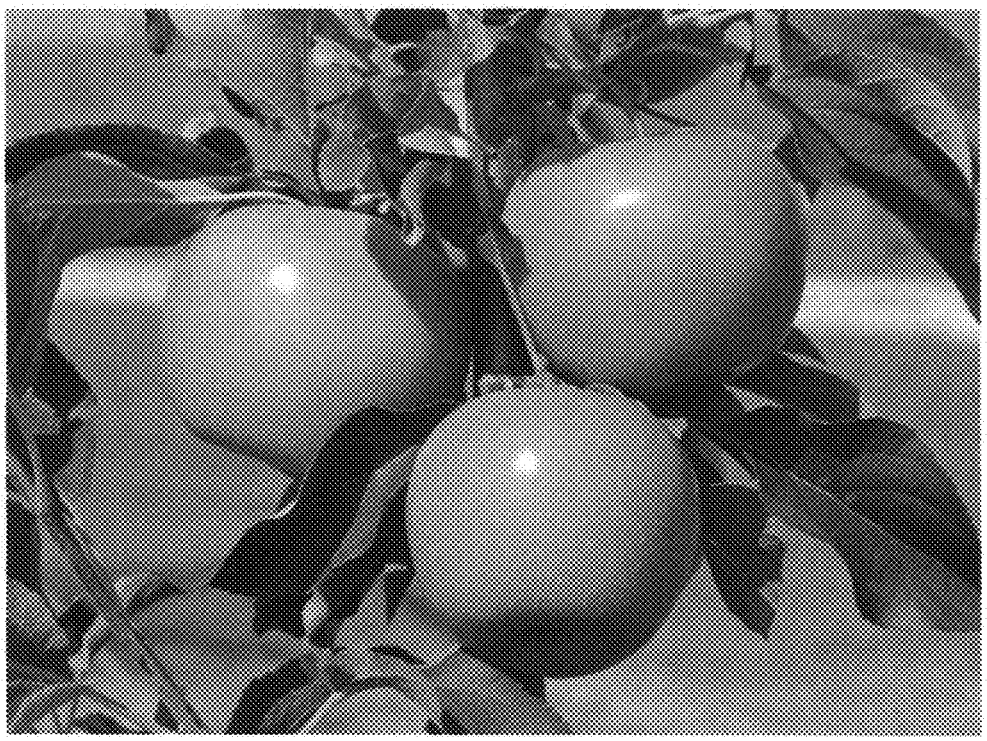
FIG. 4: illustrates the fruits of 'Smeralda'.

The new *Malus* variety 'Smeralda' has not been observed under all possible environmental conditions. The phenotype of the new variety may vary with variations in environment such as temperature, light intensity, and day length without any change in the genotype of the tree.

The aforementioned photographs, together with the following observations, measurements and values describe the new *Malus* variety 'Smeralda' as grown in the apple farm in S. Giuseppe di Comacchio (Ferrara), Italy, under conditions which closely approximate those generally used in commercial practice. The apple farm where 'Smeralda' is grown is situated near the Adriatic sea (44° 45' North, 12° 11' East) and is zero (0) meters above sea level. The soil of the apple farm where 'Smeralda' is grown is sandy, and the soil is treated with manure every year and irrigated with drip irrigation systems. The climate is temperate continental with high summer temperatures and low winter temperatures.

Unless otherwise stated, the detailed botanical description includes observations, measurements and values based on four (4) year old 'Smeralda' trees that were grown in the apple farm in S. Giuseppe di Comacchio (Ferrara), Italy, from 2007 to 2010 All trees were of cropping maturity. Quantified measurements are expressed as an average of measurements taken from a number of individual trees of 'Smeralda'. The measurements of any individual tree, or any group of trees, of the new variety may vary from the stated average.

Color references are made to The Royal Horticultural Society Color Chart (R.H.S.), except where general colors of ordinary significance are used. Color values were taken under daylight conditions at approximately at 10:00 am in S. Giuseppe di Comacchio (Ferrara), Italy.

All trees of 'Smeralda', insofar as they have been observed, have been identical in all the characteristics described below.

Classification:

*Botanical.*—*Malus domestica* Mill.

Parentage:

*Female parent.*—*Malus domestica* Mill. 'DA-85' (unpatented selection).

*Male parent.*—*Malus domestica* Mill. 'B9-5' (unpatented selection).

Propagation: Budding and grafting on M9 rootstock.

Tree:

*Age.*—Observed plants were four years old.

*Vigor.*—Medium vigor.

*Form.*—Pyramidal ramified.

*Habit.*—Spreading, branches angle is 80° to 100° with respect to trunk if allowed to grow naturally.

*Density.*—Medium density.

*Cropping behavior.*—Early beginning of production; very high and constant productivity and regular and abundant flowering; no biennial bearing.

*Type of bearing.*—Long shoot and spurs.

*Production.*—$4^{th}$ year: 15 Kg.

*Size.*—Height: 2.5 m. Spread: 1.25 m. Trunk Diameter: about 52 mm as measured 20 cm above point of grafting.

*Surface texture.*—Smooth.

*Bark color.*—Greyed-green RHS 197 A.

*Trunk lenticels.*—Length: 1.5 mm. Width: 1 mm. Color: greyed-orange, RHS 164 B. Density: 2 per $cm^2$.

*Branches.*—Number per tree: About 20 (twenty). Length: Varies due to pyramidal shape of tree. At 4 years, maximum of 90 cm to 110 cm; minimum of 10 cm to 15 cm. Diameter (at 3 years): About 8 mm to 12 mm. Surface texture: smooth. Color (at 3 years): RHS grey, RHS 201 A. Internode length: About 2 cm to 4 cm. Internode diameter: About 6 mm to 8 mm.

*Branches lenticels.*—Length: 0.5 mm. Width: 0.7 mm. Color: greyed-yellow, RHS 161 B. Density: About 5 per $cm^2$.

Leaves:

*Arrangement.*—Alternate, simple, petiolated.

*Lamina.*—Size: Length (4 year old): 91.3 mm (from $3^{rd}$ to $5^{th}$ fully expanded leaf). Width (4 year old): 52.5 mm (from $3^{rd}$ to $5^{th}$ fully expanded leaf). Length/width ratio: 1.81. Overall Shape: narrow-elliptic. Base shape: narrow to broad. Apex shape: acuminate. Margin: serrate. Pubescence: absent on upper surface and medium pubescent on lower surface. Attitude in relation to shoot: outwards. Color (mature leaves): green, RHS 139 A on the upper side and 137 C underside. Color (immature leaves): green, RHS 143 A on the upper side and 139 C underside.

*Venation.*—Type: prominent pinnate venation from a midrib to the edge. Color: light green, RHS 147 D.

*Petiole.*—Length: about 32 mm. Diameter: about 2 mm. Texture: hairy. Color: light green, RHS 147 C with medium extent of anthocyanin coloration from base, RHS 53 A red group.

*Stipule.*—Arrangement: adnate, grown together; medium size. Length (distance of stipules from basal attachment of petiole): 4 mm to 9 mm. Width: 1 mm to 1.5 mm.

Spur:

*Present.*—Yes.

*Distance between each spur.*—On the three year old branches, the distance is about 15 mm to 40 mm.

*Number of fruit per spur.*—3 to 4 with out thinning.

Flowers:

*Blooming time.*—Full bloom on April 8$^{th}$ in S. Giuseppe di Comacchio (Ferrara) Italy in year 2011.

*Blooming period.*—8 to 10 days.

*Fragrance.*—Slight.

*Type.*—Inflorescence.

*Number of flowers per inflorescence.*—5 to 6.

*Flower size.*—Diameter: about 35 mm. Flower depth (height of the corolla): about 7-8 mm, when the flower is fully open. Flower color: Primarily white, RHS 155B, when petals fully opened, undersides of petals there are shades red-purple color, RHS 70 B. In the balloon stage the color is RHS 185 C greyed-purple group.

*Buds.*—Number of buds per spur: one. Shape: pointed. Length: about 8 mm. Width: about 4.5 mm. Color: brown, RHS 200 B.

*Petals.*—Arrangement: intermediate. Number per flower: (Five to six (5 to 6)). Length: 16.95 mm. Width: 12.1 mm. Length/width ratio: 1.4. Overall shape: elliptic. Apex shape: obtuse. Base shape: rounded. Texture: smooth. Margin: entire. Color (upper surface): white, RHS 155 B. Color (lower surface): white with shade red-purple RHS 70 B.

*Sepals.*—Number per flower: five (5). Length: 3.65 mm. Width: 3.6 mm. Length/width ratio: 1.8. Overall shape: lanceolate. Apex shape: acute. Texture: hairy. Margin: entire. Color (upper surface): green RHS 143 C. Color (lower surface): green RHS 144 B.

*Pedicel.*—Length: 18 mm to 23 mm. Diameter: 2 to 3 mm. Texture: hairy. Color: green, RHS 138 B.

Fruit:

*Keeping quality.*—The fruits have a long shelf life, two weeks at room temperature.

*Maturity when described.*—Ripe for eating.

*Maturity period after full bloom.*—About 143 days in S. Giuseppe di Comacchio (Ferrara) Italy.

*Date of first and last pickings.*—About 30 August and 9 September in S.Giuseppe di Comacchio (Ferrara) Italy (North 44° 45'46.2", East 012° 11'31.9") in year 2011.

*General shape.*—Conic.

*Average weight.*—217 g.

*Fruit size.*—Average height: 68.62 mm. Average diameter (at widest point): 81 mm.

*Position of maximum diameter.*—¾ of the height near stem end.

*Height/diameter ratio.*—0.85.

*Stem.*—Length: 25.84 mm. Diameter: 2.26 mm. Color: yellow-green, RHS 152 B.

*Stalk cavity.*—Depth: 16.4 mm. Width: 38.09 mm.

*Eye basin.*—Aperture of eye: fully open. Depth: 11.1 mm. Width: 28.83 mm. Crowning at calyx end: weak. Position of sepals: erect. Calyx tube: funnel form.

*Skin.*—Thickness: medium. Texture: smooth. Bloom: absent. Greasiness: absent. Firmness (at picking time): 7 to 8 kg/cm$^2$. Overcolor color: not present. Ground color: green, RHS 144 B.

*Skin lenticels.*—Length: about 0.6 mm. Width: about 0.5 mm. Color: greyed-orange, RHS 164 B. Density: about 1.64 per cm$^2$.

*Flesh.*—Color: light-yellow, RHS 4 D. Texture: firm, crisp and juicy. Aroma: the aroma intensity is light. Eating quality: good with high level of acidity and good content in sugar. Sugar content (at picking time): 12.5 to 13.5° Brix. Acidity/Starch (at picking time): Acidity: 8 to 9 g/l Malic acid/starch: 3 Laimburg scale 1 to 5.

*Core.*—Symmetry of core: symmetric. Distinctness of core lines: clearly evident. Locules: Number (per fruit): 5 (five). Length: 12.02 mm. Width: 4.87 mm. Form: moderately open.

Seeds:

*Number per fruit.*—9 to 10.

*Number per locule.*—About 2.

*Shape.*—Ellipsoid, elongated and pointed.

*Length.*—8.86 mm.

*Width.*—5.40 mm.

*Color.*—Brown, RHS 200 D.

Reproductive organs:

*Androecium.*—Stamens: Number per flower: 20 (Twenty). Length: 6.8 mm. Filament: Length: about 6.8 mm. Anther: Shape: ovoid, flat in the center. Length: 1.96 mm. Diameter: 1.5 mm. Color: yellow, RHS 13 D. Pollen: Amount: abundant. Color: yellow, RHS 13 C. Requirements: the crab apple '*Malus* Evereste' is a good pollinator.

*Gynoecium.*—Stigma: Shape: funnel shape with receptive surface on top. Length: 0.7 mm. Width: 0.6 mm. Color: yellow-green, RHS 144 C. Style: Number per flower: 5 (Five). Length: 8.75 mm. Width: 0.35 mm. Color: yellow-green, RHS 145 B. Ovary: Length: about 3 mm. Width: about 2 mm. Color: yellow-green, RHS 144 A.

*Use.*—Fresh market.

*Sensitivity to disease/pests.*—Scab resistance.

*Winter hardiness.*—Tolerance to temperatures of −12° C. without observed damage to wood and buds of dormant apple trees; but open flowers and young fruitlets are killed by exposure to −3° C. to −5° C., depending on the length of exposure.

*Drought/heat tolerance.*—Good tolerance to heat, up to 40° C., growth is limited by drought periods without irrigation.

*Shipping/storage characteristics.*—Very good storability under ULO-conditions (1° C., 2% $0_2$, 2% $CO_2$) for up to six (6) months.

We claim:

1. A new and distinct *Malus domestica* Mill. apple tree named 'Smeralda', substantially as illustrated and described herein.

* * * * *